United States Patent [19]

Mangenet et al.

[11] Patent Number: 4,669,104
[45] Date of Patent: May 26, 1987

[54] INDICATOR FOR DETERMINING THE SENSITIVITY OF A RADIOLOGICAL DEFECT TESTING DEVICE

[75] Inventors: Gerard Y. Mangenet, Epinay Sous Senart; Jean Perruc, Bagneux; Jean F. Vaerman, Vert-Saint-Denis, all of France

[73] Assignee: Societe Nationale d'Etude et de Construction de Meteur d'Aviation-"S.N.E.C.M.A.", France

[21] Appl. No.: 797,968

[22] Filed: Nov. 14, 1985

[30] Foreign Application Priority Data

Dec. 6, 1984 [FR] France ............................... 84 18591

[51] Int. Cl.⁴ ............................................ G01D 18/00
[52] U.S. Cl. ...................................... 378/58; 378/207
[58] Field of Search .................... 378/58, 54, 89, 207; 269/234, 217; 250/252.1

[56] References Cited

U.S. PATENT DOCUMENTS

| | | | |
|---|---|---|---|
| 4,028,545 | 6/1977 | Foster | 378/207 |
| 4,055,771 | 10/1977 | Goodenough et al. | 378/207 X |
| 4,280,047 | 7/1981 | Enos | 250/252.1 |
| 4,400,827 | 8/1983 | Spears | 378/207 |
| 4,460,832 | 7/1984 | Bigham | 378/207 X |
| 4,527,057 | 7/1985 | Guyton et al. | 378/207 X |

FOREIGN PATENT DOCUMENTS 926037 4/1955 Fed. Rep. of Germany ...... 269/234
367710 1/1923 German Democratic Rep. .

OTHER PUBLICATIONS

R. McMaster: "Non Destructive Testing Handbook", vol. 1, 1959, pp. 20.36–20.38, section 20; Film Radiography, paragraph Penetrameters.

Photographic, Science & Engineering, vol. 6, No. 5, 1962, pp. 289–293; H. De Ben: "Perception of Small Detail in Industrial Radiographs".

Medical Physics, vol. 3, No. 1, Jan. 1976, pp. 19–25, New York, US; A. Jacobson: "Test Cassette for Measuring Peak Tube Potential of Diagnostic X-Ray Machines".

Primary Examiner—Frederick R. Schmidt
Assistant Examiner—Steven P. Schad
Attorney, Agent, or Firm—Bacon & Thomas

[57] ABSTRACT

An indicator for determining the sensitivity of a radiological defect testing device which simulates plane defects within a workpiece. Two or more tapered elements are placed side by side on a support such that parallel, adjacent sides define the plane defects. The elements are oriented such that the plane defect extends generally parallel to the direction of the radiation.

10 Claims, 6 Drawing Figures

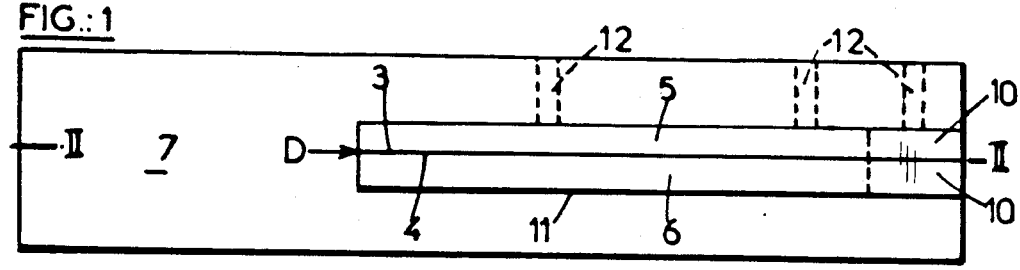
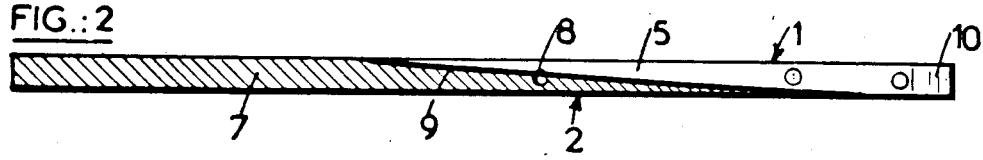
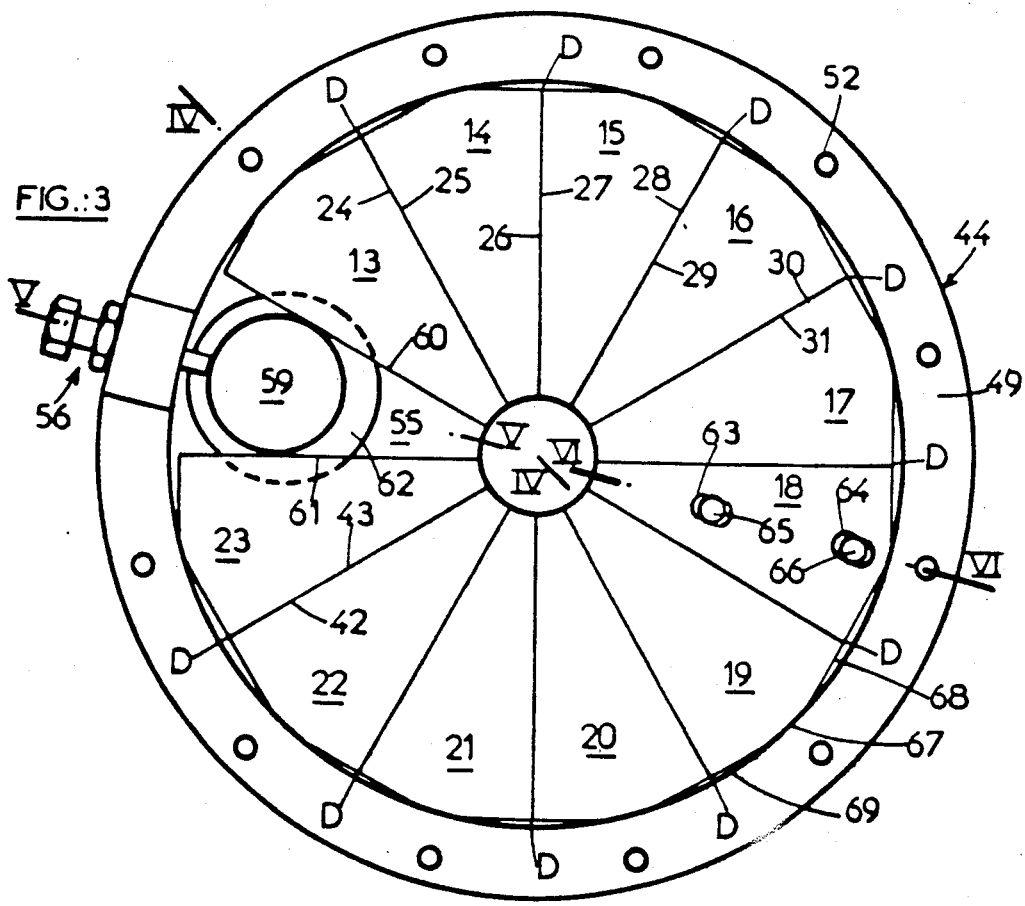

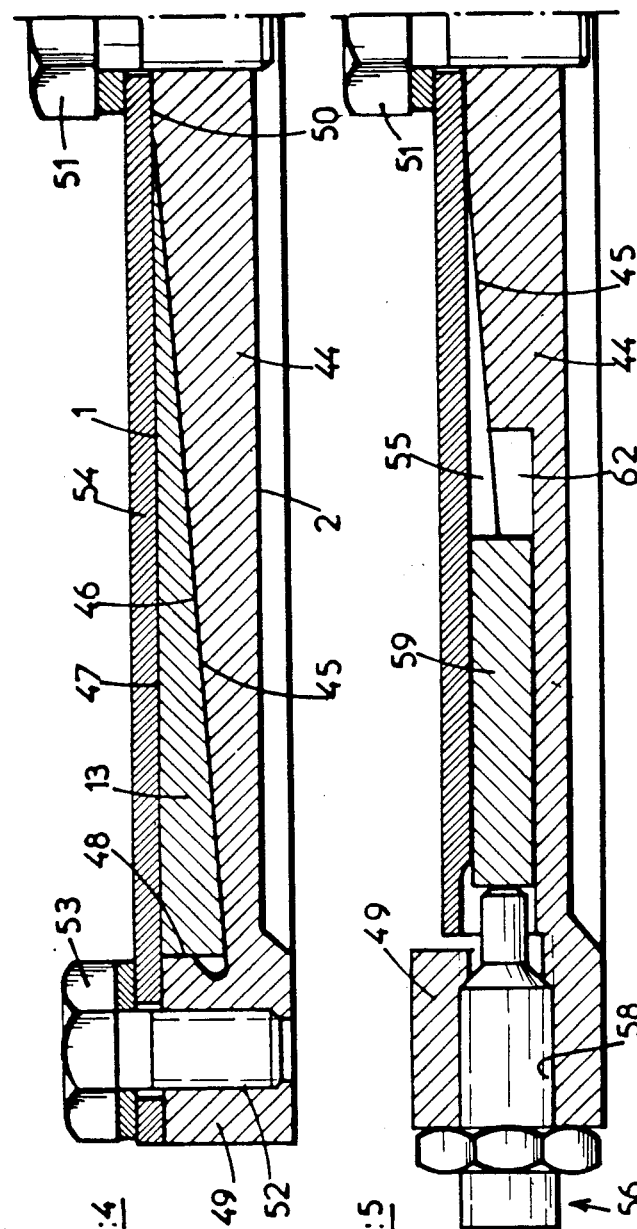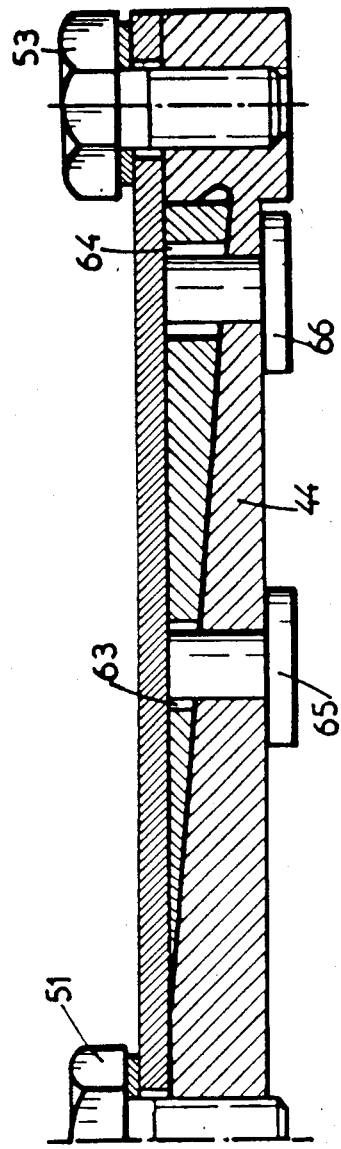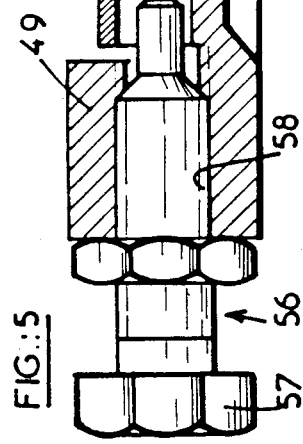

INDICATOR FOR DETERMINING THE SENSITIVITY OF A RADIOLOGICAL DEFECT TESTING DEVICE

FIELD OF THE INVENTION

This invention relates to a sensitivity indicator which is used to determine the sensitivity of a radiological defect testing device.

BRIEF DESCRIPTION OF THE PRIOR ART

It is common industrial practice to use radiological testing devices to detect defects in a workpiece. The defects may be formed during the processing of the material for the workpiece, when assembling the elements of the workpiece, or may occur during its operation. Frequently these defects take the form of an void in the material which may be caused by blisters, by an unwelded zone, or by cracks forming in the article.

When these articles are subject to inspection by radiological testing, these defects generate darker zones on the radiographic film, since they absorb less of the radiation than the remainder of the workpiece. The radiographic film may also indicate darker zones due to the change and density of the materials involved in the testing due also to the differential radiation absorption. This method of testing does not provide an image of all of the internal defects which are below a certain size relative to the thickness of the workpiece.

For a given application, it is therefore necessary to determine the detection sensitivity of the radiographic device that is utilized. The sensitivity is defined as the ratio of the smallest dimension of the defect (measured parallel to the radiation) to the thickness of the workpiece being crossed by that radiation.

Typically, the sensitivity is determined by image quality indicators which may be either the perforated type or the wire type. The perforated type of indicators consist of a metal piece with one or more ranges having parallel sides in a given thickness. One or more axial holes are formed perpendicular to the sides and are of a diameter frequently equal to the thickness of the segment to be tested. These indicators are used in the French AFNOR system and adequately represent volume defects such as blisters.

Wire type indicators consist of one or more wires having a specific diameter and with a length comparatively large with respect to their diameter. These indicators are used in the German DIN system or the English BS system.

Indicators of these types are placed on the workpiece to be examined and the smallest diameter hole or wire visible on the radiogram is determined. The sensitivity is then determined by the formula:

$$S(\%) = 100 \, \phi / E$$

where:
  S = the sensitivity
  $\phi$ = the hole or wire diameter
  E = the workpiece thickness The lower the sensitivity, the higher the picture quality. Although they are relatively easy to use, the perforated type or wire type indicators suffer from many drawbacks. These indicators are of little value in testing thin workpieces, since the wires or holes must have an excessively small diameter. The indicators also have little response to variations in the testing parameters, i.e., the size of the radiation source, the distance between the source and the workpiece, the workpiece thickness, the nature of the material, the radiation intensity, etc. Furthermore, since the holes or wires must be of discrete diameters, the indicators do not provide a continuous indication of the change in detection sensitivity. Finally, these indicators display sensitivity values without significance where defects such as plane cracks, bad welds, etc. are involved.

SUMMARY OF THE INVENTION

The instant invention provides a sensitivity indicator which simulates a plane defect which permits its use for accurately determining the sensitivity relative to thin workpieces. The indicator also strongly responds to variations in the test parameters and permits a continuous quantification of the sensitivity level. In one of the embodiments of the invention, the device may be utilized without accurately determining its position with respect to the radiation source.

The sensitivity indicator according to the invention is not placed upon the workpiece as are the prior art devices, but provide a material and thickness which corresponds to those in the workpiece to be tested. The sensitivity indicator consists of at least two elements, each of variable thickness and of similar material which are mounted on a support member of complementary thickness. The two elements are arranged side by side such that their adjacent parallel sides form the plane defect. The parallel and adjacent sides are perpendicular to the surfaces of the elements and to a surface on the support.

BRIEF DESCRIPTION OF THE DRAWINGS

FIG. 1 is a top view of a first embodiment of the sensitivity indicator according to the invention.

FIG. 2 is a side, sectional view taken along line II—II in FIG. 1;

FIG. 3 is a top view of a second embodiment of the sensitivity indicator according to the invention.

FIGS. 4–6 are partial, sectional views taken along lines IV—IV, V—V and VI—VI in FIG. 3.

DETAILED DESCRIPTION OF THE PREFERRED EMBODIMENTS

FIG. 1 shows a top view of a first embodiment of the invention which simulates a plane defect D similar to a void in the material to be tested which extends in a plane parallel to the direction of the radiation. The defect plane D is defined perpendicularly to the entry surface 1, through which the radiation enters, and the exit surface 2, from which the radiation exits. This particular arrangement corresponds to the conditions necessary to detect a defect plane of very small width. The width is defined between the parallel and adjacent sides 3, 4 of elements 5 and 6 each having a variable thickness (i.e., the dimension measured in the direction parallel to the radiation direction). The variation in thicknesses allows the device to simulate a variable depth defect plane with respect to the total thickness dimension between the entry surface 1 and the exit surface 2. The elements 5 and 6 are mounted on a support member 7 such that their generally tapered surfaces 8 are in contact with a similarly tapered surface 9 formed on the support member 7. The generally tapered surfaces 8 formed on elements 5 and 6 and the complementary tapered surface 9, formed on the support member 7 extend perpendicular to the planes of the adjacent sides 3 and 4 of the elements 5 and 6, which form the defect plane.

The variable thickness elements 5 and 6 comprise generally a right-triangle shape when viewed from the side and may have a parallelipedic extension 10 of a thickness equal to that of the thickness between the entry surface 1 and the exit surface 2 extending from the base of the triangle. The variable thickness elements 5 and 6 are mounted in a recessed portion 11 formed in support 7 such that their oblique surfaces 8 bear against the complementary surface 9. The entry surface 1 and the exit surface 2, which are perpendicular to the bases of the elements 5 and 6 are mutually parallel and form the entry and exit surfaces for the radiation. Fastener and clamping means 12 are provided on at least one side of the support 7 to retain the elements 5 and 6 within the recess 11 and to keep the adjacent sides 3 and 4 in contact with each other. The tapered configuration of the elements 5 and 6 allow a continuous variation of the defect thickness to be detected.

Instead of being continuously tapered, the elements 5 and 6 can be formed in discrete variations, such as steps, along their lengths. Similarly, the support member 7 would also be formed such that surface 9 has complementary stepped variations.

FIGS. 3-6 show an alternative embodiment of the sensitivity indicator according to the invention. This structure is insensitive to the angular position with respect to the radiation source since it defines a plurality of defect planes, each extending radially from a center. Thus, even if the device is not precisely oriented perpendicular with respect to the radiation source, at least one of the defect planes will be in alignment with the radiation direction so as to define the defect plane. The properly aligned plane will show up on the radiogram as a zone larger than the others, and this can be used in determining the sensitivity.

As shown in FIG. 3, the indicator defines six defect planes which extend in a generally radial direction from the center of the indicator. Each defect plane D is defined by the adjacent surfaces 24, 25 . . . 42, 43 of the elements 13-23. Each of the elements 13-23 is generally sector shaped and arranged side by side on a support member 44 which is generally circular in shape and has a complementary thickness. As in the previous embodiment, each of the elements 13-23 have a generally right-triangle shape when viewed from the side and are oriented such that one of the acute angles extends toward the center of the indicator, as shown in FIG. 4.

The support member 44 defines a circular conical surface 45 onto which the sector elements are mounted. Tapered surfaces 46 of the elements bears against conical surface 45 formed on the support. The tapered surface 46 and the conical surface 45 have complementary shapes such that the opposite side 47 of the sector element extends generally parallel to the exit surface 2 formed on the support member 44.

Rim 49 is attached to support member 44 and extends substantially around the perimeter of the support member. The interior surface of the rim 49 forms a surface against which the base 48 of the sector elements bears. The center of the support member 44 has a planar portion 50 extending around a threaded hole which receives the clamping means 51, which may be a bolt or the like. The rim 49 is also provided with a plurality of threaded holes 52, each of which receives a clamping means 53, which may also be a bolt. The clamping means 51 and 53 cooperate with a plate 54, which extends over each of the sector elements to retain the sector elements clamped onto the support member 44.

As best seen in FIG. 3, the sector elements 13-23 do not occupy the total space on the conical wall 45, but leave a free sector shaped area 55. A generally cylindrically shaped clamping member 59 having a generally circular cross section is placed within a recessed area 62 formed on the surface 45 of support member 44 such that a portion of its periphery bears against radial walls 60 and 61 formed on sector elements 13 and 23, respectively. The recess 62 is significantly larger than the cross section of clamping member 59 so as to allow the clamping member to move in a radial direction. An adjusting means 56 is provided on the rim 49 to adjust the radial position of clamping member 59. As shown in FIG. 5, adjusting means 56 has a screw threaded element 57 which engages the threaded hole 58 formed on the rim 49. A portion of the screw member 57 extends radially inwardly of the rim and bears against the periphery of clamping member 59. Thus, as can be seen, as screw member 57 is rotated, clamping member 59 is moved radially inwardly to exert a force on sides 60 and 61 of the sector elements 13 and 23. This forces all of the adjacent side walls of the sector elements into contact with each other.

In order to assure the proper positioning of the sector elements during clamping, the sector element 18, located diametrically opposite the clamping member 59, is provided with elongated slots 63 and 64 extending through its thickness. Studs 65 and 66 attached to the support member 44 extend upwardly into these slots so as to allow slight radial movement of this sector, but prevent any movement in a circumferential direction.

The friction between the interior portion of the rim 49 and the outer portion of the sector elements 13-23 may be reduced by forming the sector pieces such that a cylindrical central portion 67, of relatively small width, is flanked by two symmetrical plane portions 68 and 69. These symmetrical plane parts and corresponding plane parts of adjacent sector elements form planes which are located a smaller distance from the center of the support member 44 and the radius of curvature of the rim 49. This not only allows a reduction in friction but assists in the proper positioning of the sector elements 13-23.

The width of the defects in the indicator according to the invention is determined by the surface condition of the sides of the sector elements and by the tightness with which they are clamped. The defects simulated in this manner are particularly narrow and cannot easily be achieved using known indicators. However, wider defects can be obtained by interposing calibrated shims between the sides of the sector elements which form the defect planes. The indicator thickness can also be increased by placing it on a plate made of the same material in order to use this indicator with thicker workpieces.

The foregoing description is provided for illustrative purposes only and should not be construed as in any way limiting this invention, the scope of which is defined solely by the appended claims.

What is claimed is:

1. An indicator for determining the sensitivity of a radiological defect testing device comprising:
    (a) a support member having a generally planar exit suface and an opposite surface defining the thickness of the support member therebetween, at least a portion of the opposite surface defining a generally tapered portion of diminishing thickness;

(b) at least one pair of elements, having a thickness complementary to the thickness of of the support member, generally planar entry surfaces, generally tapered surfaces opposite the entry surface, and at least two planar sides defining a defect plane therebetween of varying thickness and extending generally perpendicular to the entry surface; and, (c) attaching means to attach the at least one pair of elements to the support member such that their generally tapered surfaces are in contact with generally tapered portions of the support member, their entry surfaces are generally coplanar and extend generally parallel to the exit surface of the support member, and their planar sides are parallel to and face each other so as to form the defect plane.

2. The sensitivity indicator according to claim 1 wherein the generally tapered portion of diminishing thickness is formed by a recess in the support member and the attaching means attaches the pair of elements within the recess.

3. The sensitivity indicator according to claim 2 wherein the attaching means attaches the elements to the support member such that their planar sides are in contact with each other.

4. The sensitivity indicator according to claim 1 wherein the support member is circular in shape and wherein the opposite surface forming the generally tapered portion of diminishing thickness is in the general shape of a circular frustum of a cone.

5. The sensitivity indicator according to claim 4 wherein each element has a pair of planar side walls which converge toward one end of the element.

6. The sensitivity indicator according to claim 5 wherein the attaching means attaches a plurality of elements to the frusto-conical surface of the support member such that adjacent planar side walls form defect planes radiating from the center of the support member.

7. The sensitivity indicator according to claim 6 wherein the attaching means comprises: a rim attached to the periphery of the support member; and clamping means engaging the rim and a plurality of elements to clamp the elements to the support member such that side walls of adjacent elements are in contact with each other to form the defect planes.

8. The sensitivity indicator according to claim 7 wherein the clamping means comprises:
(a) a cylindrical clamping member disposed on the frusto-conical surface of the support member between a pair of elements such that the clamping member bears against a portion of one of the side walls of each element; and,
(b) an adjusting member extending through the rim of the support member and contacting the clamping member so as to adjust the radial position of the clamping member on the support member.

9. The sensitivity indicator according to claim 8 wherein the adjusting member threadingly engages the rim of the support member.

10. The sensitivity indicator according to claim 9 further comprising:
(a) at least one elongated slot defined by an element located diametrically opposite the clamping member; and,
(b) at least one stud attached to the support member such that it extends into the elongated slot.

* * * * *

UNITED STATES PATENT AND TRADEMARK OFFICE
CERTIFICATE OF CORRECTION

PATENT NO. : 4,669,104

DATED : May 26, 1987

INVENTOR(S) : MANGENET ET AL.

It is certified that error appears in the above-identified patent and that said Letters Patent is hereby corrected as shown below:

Column 1, line 17 "an void" should be --a void--.

Signed and Sealed this

Third Day of November, 1987

Attest:

Attesting Officer

DONALD J. QUIGG

Commissioner of Patents and Trademarks